(12) United States Patent
Cornelis et al.

(10) Patent No.: US 11,454,627 B2
(45) Date of Patent: Sep. 27, 2022

(54) SENSOR

(71) Applicant: KATHOLIEKE UNIVERSITEIT LEUVEN, Leuven (BE)

(72) Inventors: Peter Cornelis, Heverlee (BE); Mehran Khorshid, Heverlee (BE); Gideon Wackers, Korbeek-Lo (BE); Patrick Wagner, Vilvoorde (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 97 days.

(21) Appl. No.: 16/480,188

(22) PCT Filed: Jan. 26, 2018

(86) PCT No.: PCT/EP2018/052021
§ 371 (c)(1),
(2) Date: Jul. 23, 2019

(87) PCT Pub. No.: WO2018/138299
PCT Pub. Date: Aug. 2, 2018

(65) Prior Publication Data
US 2020/0284813 A1    Sep. 10, 2020

(30) Foreign Application Priority Data
Jan. 26, 2017    (GB) ..................................... 1701291

(51) Int. Cl.
*G01N 33/543* (2006.01)
*G01N 25/48* (2006.01)
(Continued)

(52) U.S. Cl.
CPC ....... *G01N 33/543* (2013.01); *G01N 25/4873* (2013.01); *G01N 33/5308* (2013.01);
(Continued)

(58) Field of Classification Search
None
See application file for complete search history.

(56) References Cited

U.S. PATENT DOCUMENTS

| 5,424,219 A | * | 6/1995 | Jirikowski | ......... | G01N 33/5436 |
| | | | | | 435/4 |
| 2008/0056946 A1 | * | 3/2008 | Ahmad | .................. | G01N 33/64 |
| | | | | | 422/68.1 |

(Continued)

FOREIGN PATENT DOCUMENTS

| EP | 2772753 A1 | 9/2014 |
| EP | 3035055 A1 | 6/2016 |
| JP | 2009264904 A | 11/2009 |

OTHER PUBLICATIONS

Tong et al., Reexamining the 3-omega technique for thin film thermal characterization, Review of Scientific Instruments, vol. 77, 104902. (Year: 2006).*

(Continued)

*Primary Examiner* — Melanie Brown
(74) *Attorney, Agent, or Firm* — Workman Nydegger (57) ABSTRACT

A device suitable for the detection and/or characterization of target particles in a fluid is disclosed. The device comprises: at least one heating element for heating and/or measuring a temperature, the heating element comprising a core comprising at least one electrically conducting portion, an electric isolating layer provided at a surface of the core and electrically isolates the core from the sample, and a plurality of binding sites at/to which target particles can bind. The device further comprising a processing means configured to measure an electric output of the least one heating element, a change of the electric output of the at least one heating element and/or its heating power and for deriving, based thereon, a characteristic of the target particles.

17 Claims, 4 Drawing Sheets

(51) Int. Cl.
- *G01N 33/53* (2006.01)
- *G01N 33/74* (2006.01)
- *G01N 33/94* (2006.01)
- *G01N 33/553* (2006.01)

(52) U.S. Cl.
CPC . *G01N 33/54353* (2013.01); *G01N 33/54393* (2013.01); *G01N 33/553* (2013.01); *G01N 33/74* (2013.01); *G01N 33/9446* (2013.01)

(56) References Cited

U.S. PATENT DOCUMENTS

| | | | |
|---|---|---|---|
| 2010/0201381 A1 | 8/2010 | Iqbal et al. | |
| 2010/0274107 A1* | 10/2010 | Boock | A61B 5/1473 600/309 |
| 2014/0005508 A1* | 1/2014 | Estes | A61B 5/1495 600/347 |
| 2014/0015548 A1* | 1/2014 | Naughton | G01N 27/3278 324/658 |
| 2014/0242605 A1* | 8/2014 | Eersels | G01N 25/18 435/7.1 |
| 2015/0073515 A1* | 3/2015 | Turovskiy | A61N 1/28 607/101 |
| 2016/0178622 A1* | 6/2016 | Peeters | G01N 33/54373 435/7.8 |
| 2017/0016840 A1 | 1/2017 | Bourlon et al. | |
| 2017/0292950 A1* | 10/2017 | Van Grinsven | G01N 33/487 |
| 2019/0204249 A1* | 7/2019 | Van Grinsven | G01N 25/482 |

OTHER PUBLICATIONS

Van Grinsven et al., "Heat-transfer resistance at solid-liquid interfaces: a tool for the detection of single-nucleotide polymorphisms in DNA," ACS Nano, vol. 6, No. 3, Mar. 27, 2012, pp. 2712-2721.

Van Grinsven et al., "The Heat-Transfer Method: A Versatile Low-Cost, Label-Free, Fast, and User-Friendly Readout Platform for Biosensor Applications," ACS Applied Materials and Interfaces, vol. 6, No. 16, Aug. 8, 2014, pp. 13309-13318.

Peeters et al., "Label-free Protein Detection Based on the Heat-Transfer Method: A Case Study with the Peanut Allergen Ara h 1 and Aptamer-Based Synthetic Receptors," ACS Applied Materials and Interfaces, vol. 7, No. 19, May 20, 2015, pp. 10316-10323.

Murib et al., "Heat-transfer based characterization of DNA on synthetic sapphire chips," Sensors and Actuators B: Chemical: International Journal Devoted to Research and Development of Physical and Chemical Transducers, vol. 230, Feb. 10, 2016, pp. 260-271.

Cahill, "Thermal Conductivity Measurement from 30 to 750 K: the 3 Omega method," Review of Scientific Instruments, vol. 61, No. 2, Feb. 1990, pp. 802-808.

Lu et al., "A 3 Omega Method for Specific Heat and Thermal Conductivity Measurements," Review of Scientific Instruments, vol. 72, No. 7, Jul. 2001, pp. 2996-3003.

Great Britain Search Report from GB Application No. 1701291.5, dated Jun. 15, 2017.

International Search Report from PCT Application No. PCT/EP2018/052021, dated Mar. 15, 2018.

* cited by examiner

SENSOR

FIELD OF THE INVENTION

The invention relates to the field of detecting and/or characterizing target bioparticles in a sample. More particularly, the present invention relates to a system and method for performing heat-transfer measurements for detection and/or characterization of target bioparticles using a wire-shaped sensor element.

BACKGROUND OF THE INVENTION

In recent years, biosensors have become increasingly important in various scientific domains including medicine, biology, and pharmacology, resulting in an increased demand for fast and effective readout techniques. Recently a new method has been developed, the heat-transfer method (HTM), which can be used as a versatile bio sensor readout platform.

Figure 1:
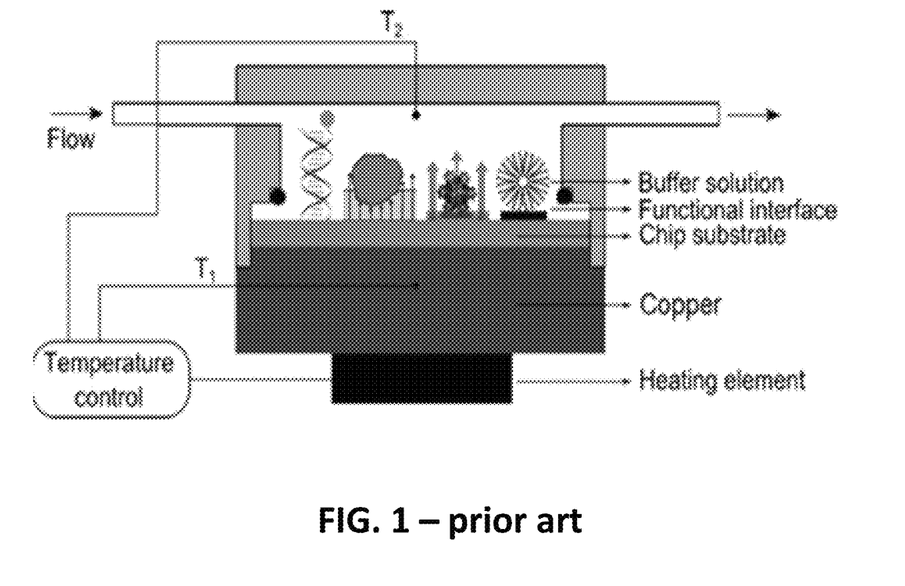
FIG. 1 schematically illustrates a known biosensor working on principles of the heat-transfer method (HTM).

A HTM setup known in the art is illustrated in FIG. 1. The central element through which the heat flux will pass consists of a chip serving as an immobilization platform onto which the functional interface is applied. This chip is pressed mechanically with its backside onto a polished copper block which serves as heat provider or heat sink. The internal temperature of the copper block, $T_1$, is measured by a thermocouple and steered via a proportional-integral-derivative controller (PID controller), connected to a power resistor. Possible heat-transfer losses between copper and the chip are minimized by conductive silver paste. The front side of the functionalized chip is exposed to the medium which contains the target of interest. An O-ring seal defines a contact area of 28 mm² between the sensing surface and the liquid. Besides of heat passing through the contact area, heat is mainly dissipated to the ambient without passing the chip surface. The temperature in the liquid, $T_2$, is measured by a second thermocouple, positioned above the solid-liquid interface. To extract the heat-transfer resistance $R_{th}$ (° C./W) quantitatively, the ratio of the temperature difference $\Delta T = T_1 - T_2$ and the input power P according to $R_{th} = \Delta T/P$, is analyzed. Thus the methodology is based on changes in heat-transfer resistance at a functionalized solid-liquid interface. To this extent, the device applies a temperature gradient over this interface and monitors the temperature underneath and above the functionalized chip in time. The heat-transfer resistance can be obtained by dividing this temperature difference by the power needed to achieve a programmed temperature.

However a major disadvantage of such a device is that only a fraction of the provided heating power is passing through the sensitive area of the chip and that the device cannot operate under flow conditions (only under steady-state conditions).

Therefore there is a need for novel and improved devices and methods.

SUMMARY OF THE INVENTION

It is an object of embodiments of the present invention to provide good devices and methods for detecting and/or characterizing target bioparticles in a sample based on heat transfer measurements. It is an advantage of embodiments of the present invention that efficient detection can be obtained. It is an advantage of embodiments of the present invention that a large fraction of the provided heating power, e.g. at least 75%, such as or example at least 85%, such as for example at least 95%, is passing through the sensing area such that an efficient system is obtained.

It is an advantage of embodiments of the present invention to provide good and efficient sensors for bio- and chemo-analytical purposes.

It is yet another advantage of embodiments of the present invention to provide good and efficient sensors for bioanalytical purposes and chemical analytics, especially aiming at a universal tool for medical diagnostics and environmental monitoring.

The above objective is accomplished by a method and device according to the present invention.

In a first aspect the present invention provides a device suitable for the detection and/or characterization of target particles in a fluid, the device comprising:
    at least one heating element for heating and/or measuring a temperature, the heating element being a wire comprising:
        a core comprising at least an electrically conducting portion,
        an electric isolating layer, said electric isolating layer provided at a surface of the core and wherein said electric isolating layer electrically isolates the core from the sample, and
        a plurality of binding sites at/to which target particles can bind;
    a processing means configured for measuring an electric output of the at least one heating element and/or a change in electric output of the least one heating element and/or a heating power of the at least one heating element, and for deriving based thereon a characteristic of the target particles. It is to be noted that a characteristic may be a presence, a type, a quantity, etc.

It is an advantage of embodiments of the present invention that a sample may be provided in liquid or gas phase. As embodiments of the present invention use heat-blocking effects, this can be applicable to materials in liquid and/or gas phase.

It is an advantage of embodiments of the present invention that the at least one heating element can be used for heating and in addition or simultaneously as a temperature sensing element for sensing a temperature of the at least one heating element. As a result only at least one heating element is needed as it may also be used as a temperature sensing element. In some embodiments, the heating and temperature sensing thus can be performed using only a single wire.

It is an advantage of embodiments of the present invention that at least one heating element can simultaneously be used as a platform where a plurality of binding sites for the target bioparticles can be provided and preferably attached.

It is an advantage of embodiments of the present invention that an additional power resistor is not needed for providing an input power and that the at least one heating element can act as a power resistor.

It is an advantage of embodiments of the present invention that thermal conductivity or thermal conductance at the surface of the core, which is contact with the sample, diminishes when bioparticles are bound with the binding sites provided on the surface. Or when bioparticles, which are bound with binding sites, sustain a change or perturbation this is reflected in the thermal conductivity or thermal conductance. Concluding, a change of the thermal conductivity/conductance advantageously provides a measure for samples of interest.

For example, the heat transfer from the heated wire to the area which is in contact with the sample (liquid or gas)

changes as a function of the presence, or absence, or special properties of the bio-particles that are bound on the wire. In most cases, such as proteins or cells, we assume that their presence on the wire impedes heat dissipation and hence the thermal conductance reduces between wire and liquid or gas. Or conversely that the "thermal resistance" increases between wire and medium.

In preferred embodiments the core has a diameter of maximum 150 µm, e.g. maximum 100 µm, e.g. maximum 25 µm, e.g. maximum 10 µm, and more preferably in the nanometer range.

In some preferred embodiments the core is completely made of an electrically conducting material, like for example material from a group consisting of metals and their alloys, precious metals, carbon nanotubes, semiconductors, boron nitride or a combination thereof.

In alternative preferred embodiments a part of the core is made of electrically non-conducting material. Furthermore, the at least an electrically conducting portion comprises a conductive coating on which the electric isolating layer is provided. The conductive coating may for example be a gold layer. In further preferred embodiments the electrically conductive coating is a material from a group consisting of metals, metal alloys, precious metals, carbon nanotubes, semiconductors, boron nitride or a combination thereof.

It is an advantage of embodiments of the present invention that a core consisting of e.g. glass fibers which are electrically non-conductive, comprising an electrically conducting material, e.g. metal coating, can be used such to enable a more economical and efficient solution.

In preferred embodiments, the electric isolating layer is made of oxides, carbides, nitrides, polymers such as for example thin polymer coatings, thiols or silanes. In some embodiments, the electric isolating layer also may be formed by a natural oxide. In preferred embodiments the plurality of binding sites at/to which target bioparticles can bind are provided directly or indirectly on the electric isolating layer. In further preferred embodiments the device, preferably a bio-sensing device, further comprises a fluid compartment for exposing the surface of the at least one heating element to a fluid sample, the at least one heating element being positioned in the fluid compartment.

In preferred embodiments the device is a dipstick device adapted for dipping at least part of the at least one heating element into a fluid sample. The device may be made without a sample container, although in dipstick devices also a sample container can be present. Dip-stick devices can be handled easily in any kind of container for the liquid under study. It is an advantage of dipstick device configurations that there is no need for a pump, thus rendering the system less complex.

In preferred embodiments the at least one heating element comprises a regular shape like e.g. cylindrical, square or triangular cross-section.

In preferred alternative the at least one heating element comprises an irregularly shaped cross-section.

In preferred embodiments wherein the surface of the at least one heating element, and more preferably the core, is roughened.

It is an advantage of embodiments of the present invention that by roughening the at least one heating element adhesion with surrounding materials may be enhanced. In addition, an enlarged surface area at the contact between the at least one heating element and the sample, where the thermal flow passes, is obtained.

In preferred embodiments the at least one heating element is suspended.

In some embodiments, the at least one heating element may comprise a curved portion along the wire.

In some embodiments, the at least one heating element may comprise a spiral shaped portion along the wire.

In some embodiments, the plurality of binding sites at/to which target particles can bind may be one or more of single-stranded DNA, aptamers, antibodies, and molecularly imprinted polymers, including also surface imprinted polymers.

In some embodiments, the processing means may be adapted for performing a 3ω frequency analysis.

In a second aspect the present invention provides methods for detecting and/or characterizing of target particles in a fluid, the method comprising:
providing at least one heating element for heating and/or measuring a temperature, the heating element comprising:
a core and
an electric isolating layer, said electric isolating layer provided at a surface of the core and wherein said electric isolating layer electrically isolates the core from the sample, and
a plurality of binding sites at/to which target particles can bind;
providing a processing means configured to measure an electric output of the least one heating element and/or its heating power and based thereon deriving a characteristic of the target particles.

In another aspect, the present invention relates to a method for detecting and/or characterizing of target particles in a fluid, the method comprising:
allowing a wire shaped heating element to interact with a fluid, the heating element comprising a core comprising at least an electrically conducting portion, an electric isolating layer and a plurality of binding sides to which the target particles can bind, —heating the wired shaped heating element,
measuring an electric output of the at least one heating element or a change thereof of the at least one wire shaped heating element and/or its heating power, and
deriving a characteristic of the target particles based on the measured electric output of the at least one heating element or change thereof or of its heating power.

In a third aspect the present invention provides heating elements for heating and/or measuring a temperature used in a sensor, the heating element comprising:
a core,
an electric isolating layer, said electric isolating layer provided at a surface of the core and wherein said electric isolating layer electrically isolates the core from the sample, and
a plurality of binding sites at/to which target particles can bind.

The heating elements thus form a sensor element that typically will be replaced or regenerated with each analysis. The other components, standard and optional, as described in the device according to embodiments of the first aspect can be re-used.

Embodiments of the present invention simplifies the concept of HTM by integrating the temperature sensors, the active sensor surface, and the heating element in just one heating element e.g. a single wire. Especially, the active sensing area and the heated surface are identical, which is not the case with HTM methods known in the art.

Embodiments of the present invention provide a wire or heating element which is electrically isolated or insulated from the sample e.g. a liquid usually an electrolyte, using a thin but dense oxide layer such as aluminum oxide or titanium oxide, which are both known for their chemical and thermal stability. This oxide layer may be fully covered by silanes (forming a self-assembling monolayer), which serve as linker molecules: In the next step, bio-chemical receptors will be coupled to the linker molecules and possible receptors include single-stranded DNA, aptamers, antibodies, and molecularly imprinted polymers. In some embodiments, also polymer coatings can be used for electrical insulation and for binding, e.g. using molecular imprinted polymer receptors. In further embodiments wires made of or comprising semiconductors such as silicon can be considered, in this case surrounded by oxides or nitrides for electrical insulation purposes, followed by a top layer of self-assembling linker molecules. Wires of noble metals such as gold and platinum are potentially also useful, provided that the self-assembling thiol monolayers (which serve as linker layers for immobilizing receptors) offer a sufficiently high electrical insulation between the wire and the surrounding liquid.

Some particular examples of receptor-target combinations are aptamer receptors targeting protein molecules and low-weight molecules, single-stranded DNA that hybridizes with complementary or mismatched target-DNA fragments and molecularly imprinted polymer layers binding small molecules, proteins, entire cells, viruses and bacteria.

The receptor layer can for example be installed around the wire from self-assembly and/or electrochemical polymerization.

In preferred embodiments the wire is suspended freely in a flow-through sensor cell, whereby all functionalization steps mentioned so far can advantageously be performed directly inside the sensor cell: generation of the isolating oxide layer, binding of the silane linkers, and tethering of the receptor functionalities. One can also consider to employ gold wires, platinum wires or silver wires, provided that the layer of linker molecules can be made sufficiently dense to isolate the core of the wire electrically from the surrounding electrolyte. The self-assembling monolayer of linker molecules will then be made of thiols instead of silanes.

In embodiments the device may further comprise a thermocouple and an additional electrode. The electrode may be used to verify that there is no electrical leaking between the wire and the sample (e.g. electrolyte) while the thermocouple may serve as an additional control for the temperature of the liquid. In alternative embodiments one can probe the temperature of the sample e.g. liquid via the resistance of the wire using a sufficiently small probe current which does not cause Joule heating.

Due to the small diameter of the heating element or wire, in embodiments several functionalized sensor wires can be installed in parallel. The second wire can be used for reference purposes (e.g. to monitor the temperature of the liquid) and, by driving both wires alternatingly, one can advantageously rule out cross-talk effects and Lorentz forces.

The recognition and binding of target molecules to the receptors surrounding the wire is expected to cause a heat-blocking effect in analogy to the observations with HTM. As a result, the required heating power (being proportional to the square of the current I providing the Joule heating) will drop while the wire temperature is kept constant at a pre-defined value. In this sense, the heating current I is the output parameter of the device, which will change during (and after) the recognition of target molecules and other bio-particles such as bacteria or cells. In contrast to HTM, the hot-wire device can be used also in flowing liquid, with the most easy situation that the flow-rate and liquid-temperature are constant.

Furthermore, the radial symmetry of the wire should allow to operate the device in all possible orientations of the flow-through sensor cell and the wire itself without an impact on the absolute value of the output data.

In preferred embodiments the wire comprises a substantially constant circular cross section.

The Hot-Wire Technique does not require thermocouples and a power resistor and the only spare part is the wire itself, which is cost-efficient.

In further preferred embodiments the wire can be seen as part of a cartridge which can easily be substituted.

The basic principle of operation of devices according to some embodiments of the present invention is the heat transfer from the heated wire to the surrounding fluid (sample). In some embodiments, the heat transfer is a function of the fluid velocity. Thus a relationship between the fluid and the electrical output can be established. The purpose of the processing means, e.g. an electronic circuit, is to provide to the wire a controlled amount of electrical current (by controlling the heating power), and in the constant temperature method, to vary such a supply so as to maintain the wire temperature constant, when the amount of heat transfer varies.

In some embodiments where a thermal wave technique is used, the electronics may be fitted to use an optimal triggering frequency and current and can be integrated into a simplified, pocket-size device.

Embodiments of the present invention can for example be used, without limiting the invention thereto, in at least five established bio(mimetic) sensor applications: (i) mutation analysis in DNA sequences, (ii) cancer cell identification and bacterial detection through surface-imprinted polymers, (iii) detection of neurotransmitters with molecularly imprinted polymers, (iv) detection of proteins and small molecules with aptamers, molecularly imprinted polymers and antibodies, and (v) phase-transition analysis in lipid vesicle layers.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a plurality of binding sites at/to which target particles can bind, this may refer to binding sites to which the target particles can directly bind or indirectly bind e.g. using a third intermediate particle.

In a first aspect, the present invention relates to a device suitable for the detection and/or characterization of target particles in a fluid. Characterization thereby may comprise identification of target particles, but also may include quantification of target particles. The target particles may be any particles of interest or particles that can act as a carrier and to which other particles of interest can be bound.

According to the first aspect, the device comprises at least one heating element for heating and/or measuring a temperature. The heating element according to the present invention is a wire comprising a core comprising at least an electrically conducting portion and an electric isolating layer, said electric isolating layer provided at a surface of the core wherein said electric isolating layer electrically isolates the core from the sample. The heating element also comprises a plurality of binding sites at/to which target particles can bind. The device furthermore comprises a processing means or processor configured for measuring an electric output of the at least one heating element and/or a change in electric output of the least one heating element and/or a heating power of the at least one heating element. The processing means also is configured for deriving, based on the measured electric output of the at least one heating element or change in electric output of the at least one heating element or change in heating power, a characteristic of the target particles. The processing means may use a predetermined algorithm, a neural network or a look up table for deriving a characteristic of the target particles. The characteristic may be a presence, a quantity, a type, a modification or any other characteristic characterizing the target particles. Further standard and optional features and advantages will now further be described with reference to the drawings, embodiments of the present invention not being limited thereto.

Figure 2:
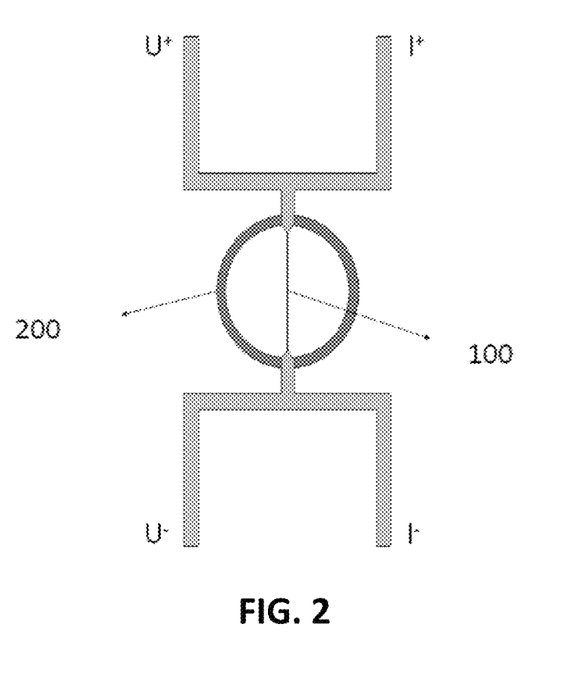
FIG. 2 schematically illustrates a device according to embodiments of the present invention where the heating element is confined with a seal.

FIG. 2 illustrates a device according to embodiments of the present invention, wherein the device comprises at least one heating element 100 for heating using a heating power, wherein the heating element comprises a core and an electrical isolating layer (not shown). The heating element 100 in this embodiment is a suspended wire, which may be referred to as a hot-wire as it is heated. The device illustrated in FIG. 2 may also comprise a seal 200, such as for example a flat seal or an O-ring seal. Furthermore the device comprises a processing means configured to measure an electric output of the least one heating element and/or its heating power and based thereon deriving a characteristic of the target bioparticles. The device of FIG. 2 preferably works as follows: the heating element or wire 100 is heated up by for example by Joule heating to a defined temperature which may be calculated by measuring the electrical resistance of the heating element 100. The thermal resistance of an empty wire (with no particles present at the binding sites) is determined by the thickness of the electrical isolating layer. Therefore, the heat will dissipate through. When particles, present in a sample one wishes to evaluate, bind at the binding sites present on the heating element 100, the thermal resistance at the solid-liquid or solid-gas interface changes, e.g. increases as a result. Measuring a parameter linked to this change, e.g. increase in thermal resistance advantageously provides properties of the sample to be evaluated. In addition, embodiments of the present invention enable that the entire outer surface of the suspended heating element or wire may serve as a sensitive area, which in this specific embodiment is confined within a seal 200. In further embodiments measuring the resistance of the wire may be performed by using an at least two-point measuring geometry. In the embodiment illustrated in FIG. 2 a four-point geometry is used which advantageously may eliminate the influence of contact resistances and thermal voltages. In addition, the at least two-point geometry, e.g. a four-point geometry, eliminates thermal voltages, provided that the current is alternating with e.g. block pulses or sinus waves. The thermal energy of Joule heating is transferred to the liquid surrounding the wire. The transfer of thermal energy from the wire 100 to the surrounding fluid, e.g. a liquid or gas sample, depends on the physical and chemical properties of the wire-to-fluid interface, in analogy with the established HTM principle.

Figure 3:
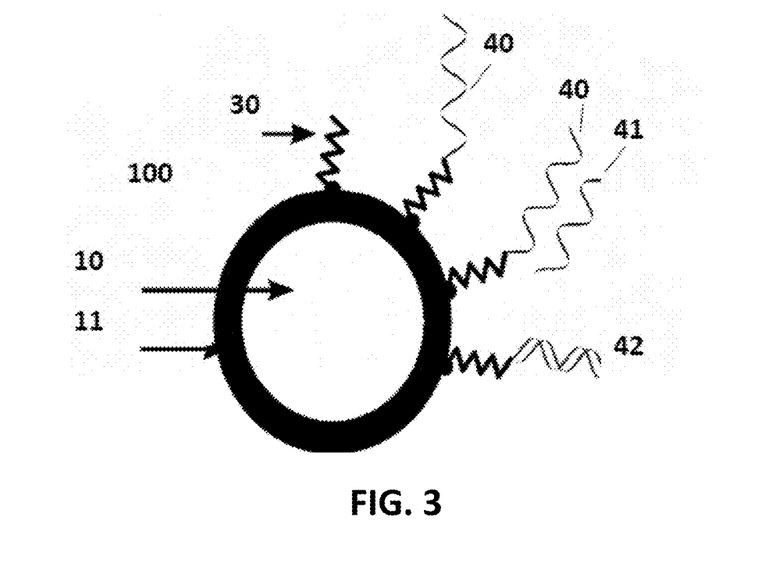
FIG. 3 schematically illustrates a cross-section of a heating element according to embodiments of the present invention.

FIG. 3 schematically illustrates a cross-section of a heating element or wire 100 according to embodiments of the present invention. The heating element comprises a core 10 and an electric isolating layer or skin 11 provided at a surface of the core wherein said electric isolating layer electrically isolates the core. The materials of the core may be chosen such that the electrical current flows through or around the core of the heating element or wire (e.g. by using a metal e.g. an aluminum or titanium core), which is electrically isolated from the surrounding sample or fluid, e.g. a liquid or gas, by a dense electrically isolating layer, e.g. oxide layer generated by for example oxidizing treatments such as annealing in air or anodization. The oxide layer may be surrounded by self-assembling linker molecules 30, preferably silane linkers. The linker molecules serve for tethering receptors to the surface of the wire, with single-stranded DNA 40, targeted DNA 41, DNA duplex 42 and aptamers as typical examples. Other core materials such as semiconductors or noble metals can be considered as well, in the latter case self-assembling layers, preferably thiol monolayers, may be used for simultaneously electrical insulation and linking of receptors. In further embodiments carbon nanotubes may be used as core material of the wire or heating element. In such embodiments the nanotubes may also be synthesized from a few other materials such as for example boron nitride. In other alternative embodiments the entire core may be an electrical conductor or an electrical isolating core with an electrically conducting coating may be used, like for example a glass fiber comprising a thin gold layer.

In preferred embodiments the heating element or wire may have a length in the order of millimeters and a diameter in the micrometer range (<0.1 mm). The wire is configured such to sustain heating up to a predefined temperature (e.g. 37° C.) by passing a controlled current (I) through or surround it (e.g. Joule heating) while the resistance of the wire is measured by using at least a two-point geometry and preferably a four-point geometry. The temperature of the wire is related to its electrical resistance and preferably monitored as a function of time. The present invention is not limited to maintaining a constant temperature of the wire but may include the possibility to measure the temperature change of the wire over time, resulting from any kind of modulation of the current (I).

Figure 4:
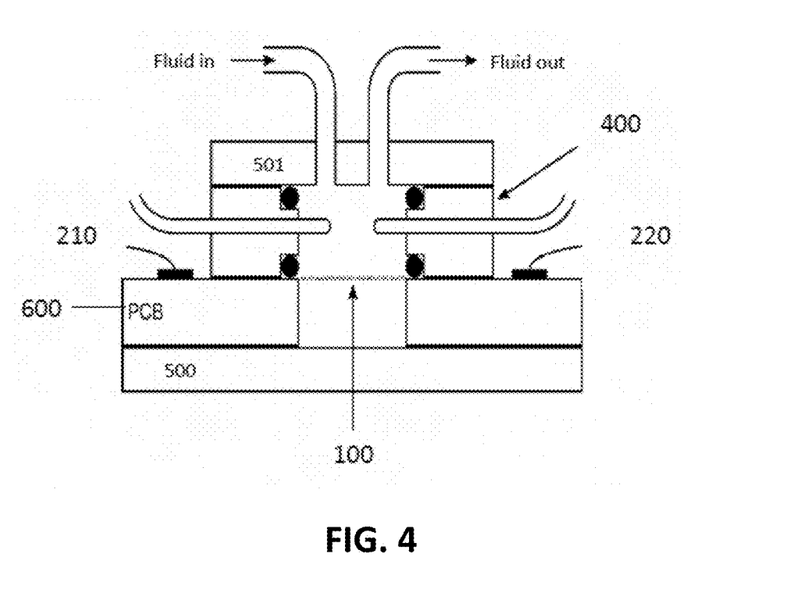
FIG. 4 schematically illustrates a device according to embodiments of the present invention.

FIG. 4 illustrates a set-up of a device according to embodiments of the present invention. In this embodiment the device comprises a flow cell 400 in which the at least one heating element or wire 100 is suspended between at least two anchoring means. The flow cell 400 comprising a channel, the channel comprising an inlet and outlet through which a fluid, e.g. liquid or gas, can flow in the flow cell 400. Suspending the wire 100 can be performed in various ways, like for example by using a magnetic field or by pulling the wire at its end in opposite directions. The wire may be anchored on a printed circuit board (PCB) 600 which is provided on a bottom substrate, preferably an optically transparent substrate like e.g. glass 500. On the PCB 600 a thermocouple 210 may be provided in addition to electrode contacts 220. The thermocouple serves as an independent temperature control inside the flow cell 400 and the electrode 220 is used to check for potential electrical shortcuts between the core of the wire and the surrounding liquid. As a result, the thermocouple and electrode are optional and not needed for the proper functioning of the device according to the present invention. The device further comprises a top optically transparent layer, e.g. glass 501, resulting in that the flow cell 400 is sandwiched in-between the top 501 and bottom glass 500. Advantageously the top- and bottom glasses may be used for inspecting the flow cell optically with respect to air bubbles and visible changes at the wire. Although in embodiments an optically transparent top layer is provided, the present invention is not limited thereto. The device of FIG. 4 may work as follows: a flow of a fluid is provided to the receptor-functionalized wire 100 which is suspended, allowing target molecules and target particles to approach the wire from all possible sides. Advantageously, there is no laminar temperature profile necessary as in case of HTM and therefor the sensor also can operate under flow conditions. A variation of the geometry can be a wire that is not suspended freely but partly supported by an underlying solid surface.

Figure 5:
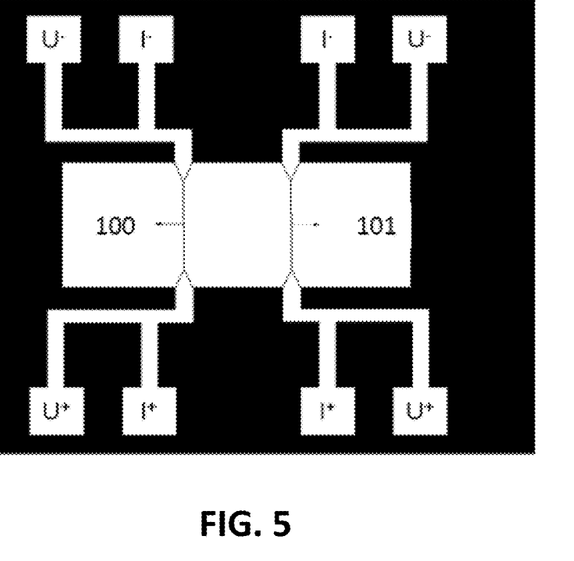
FIG. 5 schematically illustrates a top view of a printed circuit board (PCB) onto which a suspended heating elements according to embodiments of the present invention are provided.

FIG. 5 illustrates a device according to embodiments of the present invention provided as a chip. More specifically FIG. 5 illustrate a schematic top view of a PCB onto which at least one suspended hot wire 100, 101 is anchored. One wire 100 is the active wire whereas the other wire 101 serves as a reference wire. Each end of the wires 100, 101 comprises two contacts (illustrated by U- and I-). The four contacts per wire allow for sending heating currents and measuring the voltages. In this specific embodiment two suspended parallel hot wires 100, 101 are illustrated, in order to have an independent temperature measurement of the sample which may be liquid and to correct for non-specific adsorption effects of molecules and other bioparticles to the wire in case of e.g. a patient's sample.

As indicated above, embodiments of the present invention comprise a processing means or processor. Such a processor may be a dedicated processing means wherein the dedicated processing means is adapted for controlling the at least one heating element and for deriving the characteristic of the target particle. This processing device may be part of a personal computer, a smartphone or a tablet. It may be connected via a LAN, WAN or directly to the Internet. Other standard and optional features such as a memory, input channels, output channels, timers, etc. may be as well known by the person skilled in the art.

According to some embodiments, the processor may be configured for performing 3ω measurements. A particular example, illustrating such a technique—embodiments not being limited thereto—is disclosed in "Thermal conductivity measurement from 30 to 750 K: the 3ω method" by David G. Cahill in Rev. Sci. Instrum., Vol. 61, No. 2, February 1990 and in "3ω method for specific heat and thermal conductivity measurements" by L. Lu, W. Yi, and D. L. Zhang in Rev. SCi. Instrum., Vol. 72, No. 7, July 2001. By way of illustration one way to perform 3ο measurements will be described in some more detail here below. During 3-omega measurements a sinusoidal current with driving frequency omega is sent through the wire while voltage oscillations at three times this frequency are being measured. These oscillations are caused by changes in resistance of the heater, which occur at double the driving frequency. These changes, also known as Joule heating, are in turn a result of applying an ac power signal to an electrical resistor. A current source will supply the sinusoidal ac power signal at various driving frequencies while a lock-in amplifier will measure the voltage oscillations at three times the driving frequency. The amplitude of these oscillations is around three orders of magnitude lower than the voltage oscillations at the driving frequency. The precise value of the voltage and phase angle at the 3-omega frequency depends on the efficiency of heat transfer from the heated wire to the surrounding medium (mostly a liquid). This heat-transfer efficiency depends on the physical and chemical characteristics of the solid-to-liquid interface and is therefore sensitive to the binding of molecules to this interface and to changes of molecules tethered to said interface.

In some embodiments, the wire design allows also to wind the wire in the shape of a loop or even a spiralled loop such as in an incandescent glow lamp. The spiralled design makes the active area larger and increases the resistance value, thus making the measurement of the wire resistance (indicating the wire temperature) more precise.

Figure 6:
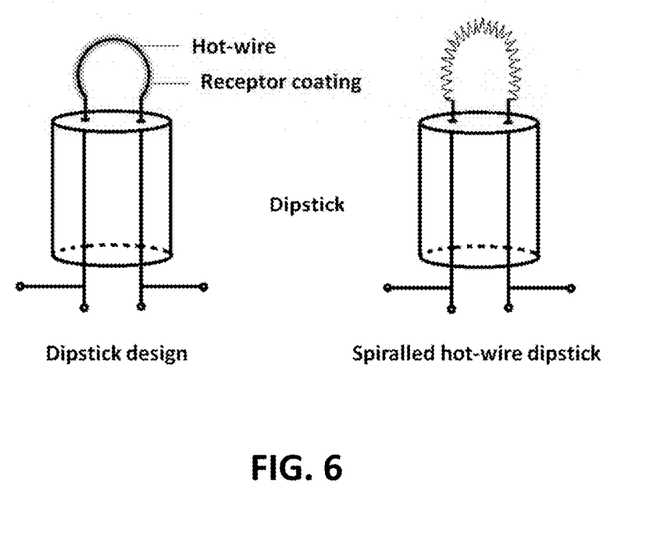
FIG. 6 schematically illustrates two devices having a dip-stick configuration, according to embodiments of the present invention.

In a particular embodiment, the device can be implemented as a dip-stick application, meaning that in principle no fluid container is required for the device itself, but that the device can be dipped into the fluid to be measured so as to identify, characterize or quantify target bioparticles of interest in the sample. A major advantage thus may exist in the fact that the sensing principle can be transferred to a simple dipstick design, making flow-through sensor cells and pumping systems obsolete. The dipstick design may especially be handy and can cope with samples with very low volumes. Two commercial biosensors, the blood-glucose test and the pregnancy test, work essentially as dipsticks, although applications are not limited to these examples. By way of illustration, embodiments not being limited thereto, an example of a dipstick embodiment is shown in FIG. 6.

Using such dipstick embodiments, dipstick assays may be performed. Such assays may for example be performed using the following subsequent steps. In a first step, the dipstick device, or more particularly the wire portion thereof, is immersed in the liquid to be tested for a given time (e.g. 3 minutes), thus allowing bio-targets to be bound to the receptor coating. In a second step, the dipstick can be immersed in clean water or a physiological salt solution with known temperature such as 20° C. This means that the conditions in the immediate vicinity of the wire are well defined, relieving any ambiguities on the factors that may influence heat transfer from the wire to its immediate surroundings.

In one aspect, the present invention also relates to a method for detecting and/or characterizing of target particles in a fluid. The method typically may comprise allowing a wire shaped heating element to interact with a fluid or more particularly the target bioparticles in the fluid. The wire shaped heating element that is used comprises a core comprising at least an electrically conducting portion, an electric isolating layer and a plurality of binding sides to which the target particles can bind. The method also comprises heating the wired shaped heating element. The method furthermore comprises measuring an electric output of the at least one heating element or a change thereof of the at least one wire shaped heating element and/or its heating power. Based on the measured electric output of the at least one heating element, the change of the electric output of the at least one heating element or the heating power used in the wire shaped heating element, a heat transfer analysis can be performed allowing to derive a characteristic of the target particles in the sample. In some embodiments, the method also may comprise, after allowing the heating element interact with the fluid, a step of contacting the heating element with clean water or a physiological salt solution with known temperature. According to some embodiments, the method thus implies using an electrically conducting wire that is covered with a receptor coating, allowing binding of analytically relevant particles to the receptor coating from a surrounding liquid. The liquid itself does not need to be electrically conducting. By sending an electrical current through the wire, Joule heating is caused and the thermal energy is transmitted to the surrounding liquid, thereby passing the receptor layer. The efficiency of the heat transfer depends on the presence or absence of target molecules captured by the receptor layer. The wire used may be used for all of the generation of the heat lux, as immobilization layer for the receptors and as a thermometer. By using, in some embodiments, the wire for these different functions, less components are required. In some embodiments, a 3-omega measurement technique is performed resulting in spreading of thermal waves into the liquid medium and allowing good detection of the heat transfer characteristics. Further steps may correspond with the functionality of elements or components as described for the first aspect.

In one aspect, the present invention also relates to a heating element for heating and/or measuring a temperature used in a sensor. The heating element comprises a core, an electric isolating layer, said electric isolating layer provided at a surface of the core and wherein said electric isolating layer electrically isolates the core from the sample, and a plurality of binding sites at/to which target particles can bind. The heating element may be connectable to a processor so as to receive control signals and send measurement data to the processor, as described in the first aspect. Further features and advantages may be as described for the heating element in the device according to embodiments of the first aspect.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

By way of illustration, embodiments of the present invention not being limited thereto, an example of a device according to a particular embodiment of the present invention will further be discussed below, to illustrate that the device can be used as bio- and/or chemical sensor based on a heat transfer principle. More particularly, the energy transfer from a heated wire to the ambient depends on the coatings around the wire. When a coating with bioreceptor properties is used, the efficiency of energy transfer depends on the binding of particles to the receptor coating. By monitoring the energy transfer, characterization of the binding particles can be performed.

In the experiment, the exemplary device comprised a heating element being a CuNi 44 (WM50) heating wire, as obtained from Heermann (Germany), having a diameter of 100 μm, with a resistivity of about 85 Ω/m. The wire was wound into coils, such that there were about 30 windings, each corresponding with a 6.35Ω resistance. The diameter of the coil was about 1 mm.

The experiments were performed using an alternating current, more particularly a sinusoidal signal, with a 90 mA amplitude at frequencies f between 10 Hz and 100 Hz. The current source used was a Keithley 6221 current source. The voltage and phase angle was measured using a Stanford Research lock-in amplifier SR850. The voltage- and phase angles where measured using a 3ω measurement technique. The resistance measurements of the wire were performed in a 4-point geometry.

Measurements were performed for a blank wire in air, a blank wire in a PBS buffer (with pH and salinity of blood plasma), a polymer coated wire in air and a polymer coated wire in a PBS buffer. The polymer coating used was a polystyrene (PS) coating with a thickness much smaller than 5 μm. A single wire was used for the experiments.

Figure 7A:
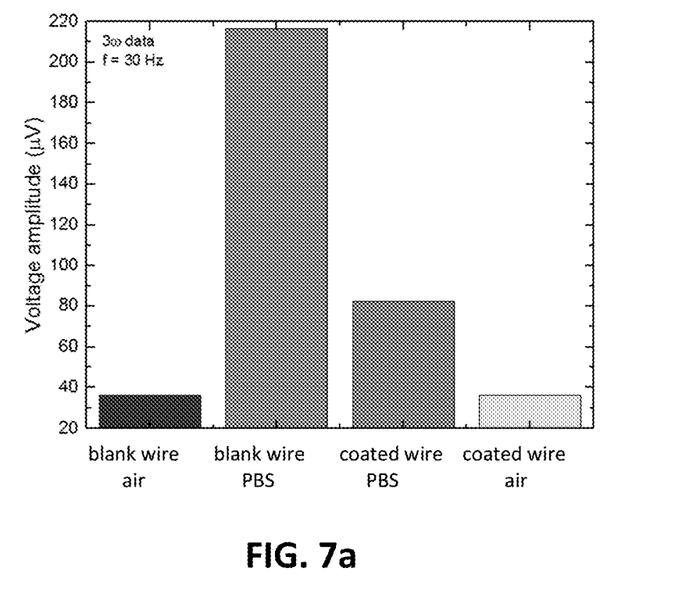
FIGS. 7a and 7b illustrate experimental results for a measurement of the voltage (FIG. 7a) and phase angle (FIG. 7b) for a heating element with and without polystyrene polymer coating, in air or PBS, illustrating features of embodiments of the present invention.
Figure 7B:
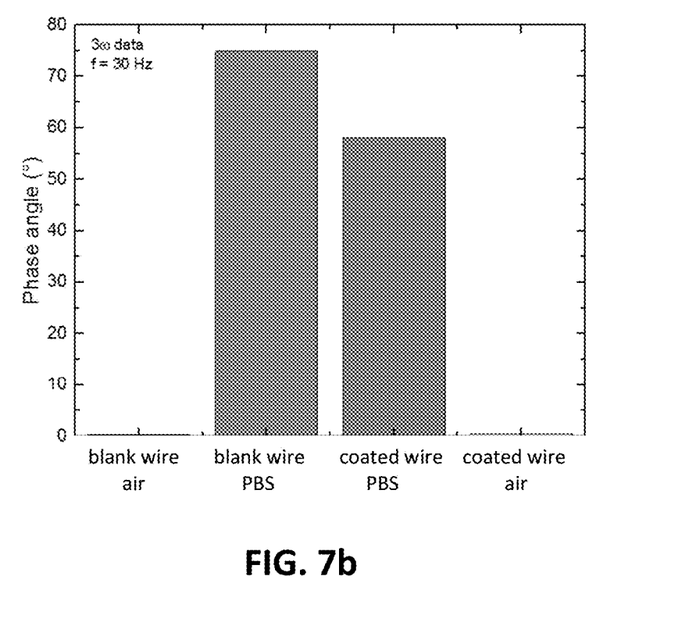

For a basic frequency f=30 Hz, the 3ω signal (90 Hz) was analysed. The results are shown in FIGS. 7a and 7b and a clear difference could be seen between both different media (air vs. PBS). Furthermore, in PBS solution also a clear difference could be seen between a blank and a polymer coated wire.

These measurements show that the efficiency of heat-transfer depends on the medium and the coating. It shows that the 3ω signals allow to discriminate situations. Furthermore they show that both the voltage amplitude and the phase angle can be used as analytical parameters.

Further by way of illustration, a number of exemplary fields of applications are discussed below, embodiments of the present invention not being limited thereto One application relates to the detection of hydrophobines in malt. Hydrophobines are induced by a fungal infection of barley and lead to an uncontrolled overflowing of the beer, rendering it unsaleable. Such hydrophobines cannot be removed from wort or beer by filtration or heat treatment. Therefore it is desirable to detect the hydrophobins in decoctions of barley and malt before commencing the brewing. The infected malt then can be rejected. For such applications, the receptors used in the device according to embodiments of the present invention may for example be molecular imprinted polymers (MIPs), antibodies or aptamer receptors. It is to be noted that the receptor layer in some embodiments may be regenerated for re-use. In some embodiments, the methods as described above may be applied.

In one application, quantitative detection of biogenic amines such as histamine in food samples is performed based on devices and embodiments according to embodiments of the present invention.

In yet another application, quantitative detection of antibiotics residues and residues of pesticides, fungicides, insecticides, herbicides, hormones and endocrine disrupters in the agricultural-, food- and water-safety sectors can be performed using devices and methods according to embodiments of the present invention. These embodiments provide cheap and portable sensing systems that may allow to provide quantitative information.

In still another application, screening of substances for narcotic drugs such as cocaine can be performed using devices and methods according to embodiments of the present invention.

The invention claimed is:

1. A device suitable for the detection and/or characterization of target particles in a fluid, the device comprising:
    at least one heating element for heating and/or measuring a temperature, the heating element being a wire that includes
        a core comprising at least an electrically conducting portion,
        an electric isolating layer, said electric isolating layer provided at a surface of the core and wherein said electric isolating layer electrically isolates the core from the sample, and
        a plurality of binding sites at/to which target particles can bind; and
    a processor that
        measures thermal resistance as an electric output of the at least one heating element and/or as a change in electric output of the at least one heating element and/or as a change in its heating power,
        derives, based on the thermal resistance as the measured electric output of the at least one heating element or the change in the electric output of the at least one heating element or the change in the heating power, a characteristic of the target particles, and
        controls the heating power of the at least one heating element by providing to the wire a controlled amount of electric current.

2. The device of claim 1, wherein the core has a diameter of maximum 100 μm.

3. The device of claim 1, wherein the core is completely made of an electrically conducting material selected from a group consisting of metals and their alloys, precious metals, carbon nanotubes, semiconductors, boron nitride and a combination thereof.

4. The device of claim 1, wherein a part of the core is made of an electrically non-conducting material and wherein the at least an electrically conducting portion comprises a conductive coating on which the electric isolating layer is provided.

5. The device of claim 4, wherein the conductive coating is a material selected from a group consisting of metals, metal alloys, precious metals, carbon nanotubes, semiconductors, boron nitride and a combination thereof.

6. The device of claim 1, wherein the electric isolating layer is made of oxides, carbides, nitrides, polymers, thiols, silanes or thin polymer coatings.

7. The device according to claim 1, wherein the plurality of binding sites at/to which target bioparticles can bind are provided directly or indirectly on the electric isolating layer.

8. The device according to claim 1, the bio-sensing device further comprising a fluid compartment for exposing the surface of the at least one heating element to a fluid sample, the at least one heating element being positioned in the fluid compartment.

9. The device according to claim 1, wherein the device is a dipstick device adapted for dipping at least part of the at least one heating element into a fluid sample.

10. The device according to claim 1, wherein the at least one heating element comprises a regularly shaped cylindrical, square or triangular cross-section.

11. The device according to claim 1, wherein the at least one heating element comprises an irregularly shaped cross-section.

12. The device according to claim 1, wherein the surface of the at least one heating element is roughened.

13. The device according to claim 1, wherein the at least one heating element is suspended.

14. The device according to claim 1, wherein the at least one heating element comprises a curved portion along the wire.

15. The device according to claim 1, wherein the at least one heating element comprises a spiral shaped portion along the wire.

16. The device according to claim 1, wherein the plurality of binding sites to which target particles can bind are one or more of single-stranded DNA, aptamers, antibodies, and molecularly imprinted polymers.

17. The device according to claim 1, wherein the processor performs a $3\omega$ frequency analysis on the wire.

* * * * *